(12) United States Patent
Sartor et al.

(10) Patent No.: US 10,980,446 B2
(45) Date of Patent: Apr. 20, 2021

(54) APPARATUS AND METHOD FOR DETERMINING A SEDENTARY STATE OF A SUBJECT

(71) Applicant: KONINKLIJKE PHILIPS N.V., Eindhoven (NL)

(72) Inventors: Francesco Sartor, Eindhoven (NL); Erik Gosuinus Petrus Schuijers, Breda (NL); Gabriele Papini, Eindhoven (NL); Louisa Simone Ruijs, Eindhoven (NL); Paul Marcel Carl Lemmens, Veghel (NL); Chantal Nathalie van den Broek, Schijndel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 162 days.

(21) Appl. No.: 15/572,526

(22) PCT Filed: May 6, 2016

(86) PCT No.: PCT/EP2016/060187
§ 371 (c)(1),
(2) Date: Nov. 8, 2017

(87) PCT Pub. No.: WO2016/180728
PCT Pub. Date: Nov. 17, 2016

(65) Prior Publication Data
US 2018/0125394 A1    May 10, 2018

(30) Foreign Application Priority Data
May 11, 2015 (EP) .................................. 15167124

(51) Int. Cl.
*A61B 5/00* (2006.01)
*A61B 5/11* (2006.01)

(52) U.S. Cl.
CPC ........... *A61B 5/1118* (2013.01); *A61B 5/1116* (2013.01); *A61B 5/7207* (2013.01);
(Continued)

(58) Field of Classification Search
CPC ... A61B 5/1118; A61B 5/1116; A61B 5/7207; A61B 5/7246; A61B 5/7264;
(Continued)

(56) References Cited

U.S. PATENT DOCUMENTS

| | | | | |
|---|---|---|---|---|
| 5,269,318 | A * | 12/1993 | Nashner | A61B 5/0488 600/595 |
| 8,436,737 | B1 * | 5/2013 | Trout | A61B 5/1116 340/573.1 |
| 9,149,222 | B1 * | 10/2015 | Zets | A61B 5/1116 |
| 2002/0156399 | A1 * | 10/2002 | Kanderian | A61B 5/0488 600/587 |

(Continued)

FOREIGN PATENT DOCUMENTS

| | | |
|---|---|---|
| JP | 2010125239 A | 6/2010 |
| WO | 2009083032 A1 | 7/2009 |
| WO | 2010026513 A1 | 3/2010 |

*Primary Examiner* — May A Abouelela (57) ABSTRACT

The present invention relates to distinguishing different sedentary states of a subject. A sedentary state can refer to standing, sitting and/or lying. An apparatus for determining a sedentary state of a subject is presented that comprises a sensor interface for obtaining a movement signal indicative of a movement of the subject; an extraction unit for extracting a signal feature indicative of postural control oscillations of the subject from the movement signal, wherein the signal feature indicative of postural control oscillations is indicative of center of mass motion oscillations for preventing the subject from falling; and a classifier for classifying a sedentary state of the subject based on the signal feature indicative of postural control oscillations of the subject. Further, a corresponding method, computer program and system are presented.

19 Claims, 3 Drawing Sheets

(52) U.S. Cl.
CPC .......... *A61B 5/7246* (2013.01); *A61B 5/7264* (2013.01); *A61B 5/7221* (2013.01); *A61B 5/74* (2013.01); *A61B 2562/0219* (2013.01)

(58) Field of Classification Search
CPC . A61B 5/7221; A61B 5/74; A61B 2562/0219; A61B 5/0488; A61B 5/486; A61B 5/14546; A61B 5/1121; A61B 5/4023; G06F 3/017; G06F 1/163; G06F 3/014
USPC .................. 600/300, 587, 595; 702/189, 141
See application file for complete search history.

(56) References Cited

U.S. PATENT DOCUMENTS

| | | |
|---|---|---|
| 2004/0112151 A1 | 6/2004 | Maxwell et al. |
| 2005/0021312 A1 | 1/2005 | Tanaka et al. |
| 2009/0137933 A1 | 5/2009 | Lieberman et al. |
| 2010/0298655 A1 | 11/2010 | McCombie et al. |
| 2010/0298661 A1* | 11/2010 | McCombie ............ G16H 50/50 600/301 |
| 2011/0152727 A1* | 6/2011 | Ten Kate ........... G08B 21/0446 600/595 |
| 2013/0123666 A1* | 5/2013 | Giuffrida .............. A61B 5/0024 600/595 |
| 2013/0184613 A1 | 7/2013 | Homsi et al. |
| 2013/0207889 A1 | 8/2013 | Chang et al. |
| 2014/0128778 A1* | 5/2014 | Chan ..................... A61B 5/1116 600/595 |
| 2014/0330171 A1* | 11/2014 | Pan ..................... A61B 5/1123 600/595 |

* cited by examiner

APPARATUS AND METHOD FOR DETERMINING A SEDENTARY STATE OF A SUBJECT

This application is the U.S. National Phase application under 35 U.S.C. § 371 of International Application No. PCT/IB2016/060187, filed on May 6, 2016, which claims the benefit of European Application No. 15167124.5, filed May 11, 2015. These applications are hereby incorporated by reference herein.

FIELD OF THE INVENTION

The present invention relates to activity tracking and in particular to an apparatus and method for determining a sedentary state of a subject.

BACKGROUND OF THE INVENTION

In the field of healthcare, fitness and leisure activities, the use of activity trackers or activity monitors for monitoring a physical activity of a subject has become more and more popular. Starting from pedometers, which count the number of steps, the technology has evolved towards more sophisticated activity trackers which distinguish between different types of physical activities such as walking, running or cycling. For example, walking and running can be distinguished from being sedentary based on a step frequency. Exemplary systems feature for example a wrist band with a sensor, wherein the wristband is in communication with a smart phone that is running a fitness tracking app.

While existing activity trackers successfully distinguish between different types of activities, such as walking and running, they do not distinguish between different sedentary states, such as standing, sitting and lying. Static sedentary body postures, such as standing, sitting and lying, are hard to distinguish by means of unobtrusive wearable devices such as motion sensors.

However, knowing whether a subject is standing rather than sitting or lying can be very relevant information in many instances. For example, pregnant women are at high risk of lower limbs edema and of developing varicose veins when standing still. In some occupations standing still is a common postural behavior, for example for hairdressers or production workers, which increases the risk for those workers of problems to the lower limbs. There can be a need to distinguish between different sedentary states and in particular to determine whether a person is standing.

As a solution, US 2004/0112151 A1 discloses an activity monitor, which distinguishes between the sedentary states standing and sitting based on an inclination of the thigh. An accelerometer has to be applied in a particular defined orientation to the thigh of the subject, i.e., to the upper leg segment. A single axis accelerometer is used as the sensor. Depending on the amplitude of the output signal of the accelerometer, the sedentary activity is classified as sitting or standing. The classification is thus based on an inclination of the accelerometer axis with respect to the gravity vector. If the subject is standing, the thigh is parallel to the gravity vector. If the subject is sitting, the thigh is substantially perpendicular to the gravity vector. The different orientations result in a different absolute value measured by the accelerometer, which is then used to distinguish between sitting and standing. The device does not distinguish between sitting and lying.

WO 2009/083032 A1, even though being related to the different technical field of early detection of Parkinson related blocking episodes, teaches a further refinement to distinguish between standing, sitting and lying. A first accelerometer is applied to the thigh of the subject and a second accelerometer is applied to a shank of the subject. Hence, a second accelerometer is applied to the lower leg segment. The system can distinguish between standing, sitting and lying based on the accelerometer readings on different axes of the employed two-dimensional accelerometers. When standing quietly, the thigh and shank are parallel to the gravity vector, such that both the accelerometers applied to the thigh and the accelerometer applied to the shank measure a vertical acceleration of 1 g. If the subject is sitting, the shank is parallel to the gravity vector and the thigh is substantially perpendicular to the gravity vector, such that the accelerometer at the shank measures a vertical acceleration of 1 g, whereas the accelerometer at the thigh measures a horizontal acceleration of −1 g. If the subject is lying, the thigh and shank are substantially perpendicular to the gravity vector, such that both the accelerometer at the thigh as well as the accelerometer at the shank measure a horizontal acceleration of −1 g. Hence, the orientation of two accelerometers applied to different segments of the leg is compared and evaluated.

Correspondingly, US 2013/0207889 A1 teaches that sitting or standing and lying down can be distinguished by the orientation of an accelerometer. An acceleration of 1 g on the accelerometer y-axis indicates sitting or standing whereas an acceleration of 0 g indicates that the user is lying down.

US 2013/0184613 A1 teaches to determine different states based on the relative position of body parts with respect to one another. Sensors are placed at different locations of the user's body to detect the individual positions of each body part.

US 2010/0298655 A1 also teaches to evaluate an orientation of a motion-detecting sensor on the patient to determine a posture parameter.

A drawback of these solutions is that one or two accelerometers have to be worn at specific body locations and that the accelerometers have to be mounted in a well-defined orientation.

SUMMARY OF THE INVENTION

Therefore, it is an object of the present invention to provide an apparatus and method for determining a sedentary state of a subject which substantially alleviates or overcomes the afore-mentioned problems. In particular, it is an object of the present invention to provide an apparatus for determining a sedentary state of a subject which can be used in several wearing positions. It can be an object that an orientation of the sensor in space and/or a location of the device on the body of the user do not have to be known beforehand. Hence, the user comfort and ease of use can be improved.

In a first aspect of the present invention, an apparatus for determining a sedentary state of a subject is presented that comprises:

a sensor interface for obtaining a movement signal indicative of a movement of the subject;

an extraction unit for extracting a signal feature indicative of postural control oscillations of the subject from the movement signal, wherein the signal feature indicative of postural control oscillations is indicative of center of mass motion oscillations for preventing the subject from falling; and a classifier for classifying a sedentary state of the subject based on the signal feature indicative of postural control oscillations of the subject.

In a further aspect of the present invention, a method for determining a sedentary state of a subject is presented that comprises:

obtaining a movement signal indicative of a movement of the subject;

extracting a signal feature indicative of postural control oscillations of the subject from the movement signal, wherein the signal feature indicative of postural control oscillations is indicative of center of mass motion oscillations for preventing the subject from falling; and classifying a sedentary state of the subject based on the signal features indicative of postural control oscillations of the subject.

In a further aspect of the present invention, a system for determining a sedentary state of a subject is presented that comprises a movement sensor, in particular an accelerometer, for providing the movement signal; and the aforementioned apparatus for determining a sedentary state of a subject.

In yet further aspects of the present invention, there are provided a computer program which comprises program code means for causing a computer to perform the steps of the method disclosed herein when said computer program is carried on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, systems, computer program and medium have similar and/or identical preferred embodiments as the claimed apparatus for determining a sedentary state of a subject as defined in the dependent claims.

The inventors have found that sedentary states, such as standing, sitting and/or lying can be distinguished and classified by evaluating subtle subconscious movements for balancing the body of the subject. While e.g. standing or sitting, any individual performs involuntary postural corrections which can be captured by a sensor. It was found that the amount of such balancing effort can serve as an indicator for distinguishing different sedentary states. Postural control oscillations are produced by the skeletal muscular system to keep the center of mass within a base of support. They are a distinctive involuntary body action in particular occurring during standing upright. The center of mass can be used to model the way a human maintains balance while standing. The postural muscles are constantly counteracting, by contractions and relaxations, any tendency of the body to move the center of gravity outside the base of support. In other words, the signal feature indicative of postural control oscillations is indicative of center of mass motion oscillations for preventing the subject from falling. The underlying concept of balancing a body in a sedentary state, i.e., in a non-moving state on a macroscopic scale, is that the center of mass has to be balanced. The movement signal obtained by the sensor interface can comprise such information indicative of a movement of the center of mass of the subject. The main postural muscles are located in the lower limbs, even though, back muscles are also involved in the postural control. Hence, even though standing still, sitting and lying down are sedentary states, postural control oscillations can be evaluated as a subtle balancing effort of the subject. For example, sitting or lying typically requires a lower postural control effort than standing upright. Postural control oscillations are typically reduced when sitting because contributions from the lower limbs are reduced or absent. Nonetheless, postural control oscillations from the torso can still be present, even though they can be less prominent. A chair with back support may further reduce postural control oscillations. Correspondingly, lying can require a lower postural control effort than sitting, up to the extent that postural control can be substantially absent while lying.

An advantage of the apparatus for determining a sedentary state according to an aspect of the present invention is that a movement sensor for providing the movement signal indicative of a movement of the subject can be arranged at different wearing positions and does not require the particular arrangement of an accelerometer at the thigh of the subject. For example, movement signals from a sensor at wearing positions such as pocket, belt, wrist, or a neck can be evaluated.

A movement signal indicative of a movement of the subject can be provided from any type of sensor capable of sensing postural control oscillations directly or indirectly such as an accelerometer, a gyroscope, a magnetometer, an electromyogram, a mechanomyogram, a pressure sensor such as an insole pressure sensor, or load cells such as a force plate, smart tile or weighing scale. Advantageously, the movement signal is able to describe a cinematic status of the body. It is not necessarily required that signal enables a precise calculation or detailed reconstruction of the movements. It can be sufficient that the movement signal is related to the postural control oscillations and can thus serve as an indicator of postural control oscillations. Advantageously, the movement signal has a sampling rate or frequency resolution higher than a frequency of postural oscillations. Postural control oscillations can typically occur at low frequencies of for example less or equal to 20 Hz, in particular less than 10 Hz, in particular less than 6 Hz, in particular less than 1 Hz. Alternatively, postural control oscillations can refer to a range of oscillations of 1 to 6 Hz. The movement signal can provide a frequency resolution or sampling rate for measuring said postural control oscillations, in particular a frequency resolution or sampling rate of at least 1 or 2 Hz, preferably at least 5 or 6 Hz, preferably at least 20 Hz, preferably at least 40 Hz can be provided. An accelerometer as an exemplary movement sensor advantageously has a range of at least ±2 g in order to fully collect possibly the whole spectrum of movement. It should be noted, that one or more sensors for obtaining the movement signal and the apparatus for determining a sedentary state of a subject can be implemented as a single device or alternatively as separate units. The units can be in communication for example via a wired or wireless link. The apparatus can also be implemented in a processing device or by devices such as a smart phone, tablet, phablet, smart watch, wrist band and/or activity tracker.

A determination of a sedentary state can be performed substantially in real time or can also be performed on prerecorded data which is obtained as a movement signal indicative of a movement of the subject via the sensor interface of the apparatus for determining a sedentary state of the subject.

A further advantage of determining a sedentary state of a subject in the sense of classifying a sedentary state in order to distinguish different types of sedentary states, is that an energy expenditure estimate can be corrected based on one or more sedentary states of the subject. For example, a subject exhibits a higher level of energy expenditure when standing compared to sitting or lying down.

Determining a sedentary state as used herein can refer to determining a sedentary state among different possible sedentary states such as standing, sitting and/or lying. Hence, determining a sedentary state can be understood as distinguishing a sedentary state or classifying a sedentary state, in particular classifying a sedentary state into at least one of standing, sitting and/or lying. Hence, the classifier can provide a discrete classification. Alternatively, the classifier can provide a probability that the user is in a particular sedentary state. Hence, the classification does not necessarily need to be discrete. For example, the classifier can provide a probability that the user is currently standing, sitting and/or lying down.

According to an embodiment, classifying a sedentary state of the subject comprises a classification into at least one of standing, sitting and/or lying.

In an embodiment, the classifier for classifying a sedentary state of the subject is configured for classifying the sedentary state as a first sedentary state, if the signal feature indicative of postural control oscillations of the subject is larger or equal to a first predetermined threshold, or as a second sedentary state, if the signal feature indicative of postural control oscillations of the subject is smaller than the first predetermined threshold. For example, the first sedentary state is standing, whereas the second sedentary state is sitting and/or lying. It should be noted, that sitting and lying can be seen as one sedentary state or alternatively can also be seen as two separate sedentary states to be distinguished. The classifier for classifying a sedentary state can optionally be further configured to take a second predetermined threshold smaller than the first predetermined threshold into account to further distinguish the second sedentary state from a third sedentary state, and so on. For example, the second sedentary state can be sitting and the third sedentary state can be lying. If the signal feature indicative of postural control oscillations of the subject is smaller than the first predetermined threshold but larger or equal to the second predetermined threshold the classifier for classifying a sedentary state can be configured for classifying the sedentary state as sitting, whereas if the signal feature indicative of postural control oscillations of the subject is smaller than the second predetermined threshold, and hence also smaller than the first predetermined threshold, the classifier for classifying a sedentary state can be configured for classifying the sedentary state as lying.

In an embodiment, the signal feature indicative of postural control oscillations comprises at least one of an oscillation amplitude, an oscillation variance, and a sum of distances of values of the movement signal from a center of a cloud of said values of the movement signal. It should be noted, that the aforementioned signal features can also refer to normalized quantities. Advantageously, the analysis can be based on an absolute value of a change in acceleration, in particular in the time domain. An advantage is that noise can have a much lower contribution according to this aspect. Advantageously, for example in the case of a three dimensional accelerometer, signals from different sensors or sensor axes can be combined in order to obtain a signal which is substantially independent of an orientation of the sensors or accelerometer in space. Thereby, the determination of the sedentary state of the subject becomes substantially independent of an orientation of the sensor.

In an embodiment the extraction unit for extracting a signal feature indicative of postural control oscillations is configured for determining signal windows in the movement signal indicative of voluntary movements; and to discard the signal windows that are indicative of voluntary movements. Advantageously, the apparatus according to an aspect of the present invention can be combined with existing approaches for determining different types of voluntary activities such as running, walking, cycling or swimming. Signal portions that are indicative of such non-sedentary actions can be discarded. In the context of the present invention, postural control oscillations can be seen as involuntary movements in terms of subconscious movements in contrast to voluntary movements for walking, running, or voluntary action such as, for example, raising a hand. For example, physical activities such as walking have a substantially larger impact on the center of mass of the subject such that this can cause large amplitudes in a movement signal. For example, signal portions above a predetermined threshold such as a predetermined oscillation amplitude can be discarded. Furthermore, a spectral analysis can be performed in order to identify voluntary movements by their spectral components or spectral footprint. In case that an accelerometer is used as the sensor, a change in the amount of gravity on one or more axes can be detected as a voluntary movement and filtered out. This case can frequently occur for a wrist-mounted accelerometer when the user is voluntarily moving his arm. Optionally, the apparatus comprises a filter for filtering out noise and/or drift, for example a band pass which filters out a slow signal drift of the sensor and high frequency noise components. Postural control oscillations can refer to low frequency oscillation in the absence of higher frequency oscillations. For example, postural control oscillations can range between 0.5 and 20 Hz, in particular between 1 and 6 Hz.

In an embodiment, extracting a signal feature indicative of postural control oscillation comprises windowing the movement signal and discarding signal windows with the variance of the movement signal above a predetermined threshold. The step can be seen as a form of preprocessing or filtering, in order to remove signal components which do not refer to postural control oscillations. A threshold can be determined by annotated data, for example, such that distributions can be built up for distinguishing voluntary from involuntary movements. The threshold can be also be personalized, in particular with a calibration phase that can be automatic or done by the user. In an embodiment, a pattern recognition approach can be used that can correctly classify voluntary movements via a machine learning approach.

In a further refinement, the extraction unit for extracting a signal feature indicative of postural control oscillations is configured for determining signal windows in the movement signal indicative of voluntary movements by determining if an amplitude and/or variance of the movement signal exceeds a predetermined voluntary movement threshold and/or by determining if a spectral content of the movement signal corresponds to a voluntary movement spectrum. For example, a spectral content relating to walking, running or cycling can be evaluated and corresponding portions of the movement signal can be discarded when determining a sedentary state of a subject, since the corresponding signal portions can already be attributed to a non-sedentary physical activity of the subject. The evaluation of the amplitude of the movement signal can relate to an absolute amplitude of the movement signal or can also be directed to a relative change of the movement signal with respect to an offset or mean value such as an oscillation amplitude. A spectral power density of at least portions of the movement signal can be evaluated to determine signal windows indicative of voluntary movements of the subject, for example by comparison to known power spectral densities of voluntary movements.

In an embodiment, the extraction unit for extracting a signal feature indicative of postural control oscillations is configured to determine a gravity vector and to determine a signal feature indicative of postural control oscillations which are substantially perpendicular to the gravity vector. An advantage of this embodiment is that a complexity of subsequent calculations can be reduced since the analysis can be limited to postural control oscillations which are substantially perpendicular to the gravity vector. The purpose of postural control oscillations is essentially preventing a subject from falling. Hence, a stabilizing movement in a lateral direction or horizontal plane can be more important than stabilization in a vertical direction. Hence, assuming that the gravity vector points in a negative y direction, it can be sufficient to evaluate postural control oscillations in x- and/or z-direction. The gravity vector can be determined by low pass filtering the output signals of a three dimensional accelerometer and determining a direction of a substantially constant acceleration of 1 g. Depending on an orientation of the movement sensor, a rotation of the coordinate system can be employed.

In an embodiment, the extraction unit and/or the classification unit comprises an adaptive threshold for extracting a signal feature indicative of postural control oscillations of the subject from the movement signal or for classifying a sedentary state based on the signal feature indicative of postural control oscillations of the subject, respectively. Advantageously, thresholds, in particular decision thresholds used in the aforementioned signal processing can be adjusted depending on the subject, for example, based on age, sex, health state or fitness, or depending on a type or location of the movement sensor, for example, if a movement signal is obtained from an acceleration sensor for example worn in a pocket of trousers arranged at a hip region, a chest pocket, at a wrist or even in a handbag. An advantage of this embodiment is that an independence of a type, orientation and/or inclination of a sensor can be further increased.

In an embodiment, the apparatus for determining a sedentary state of a subject further comprises a timing unit for determining a duration of the sedentary state; and an alert unit for providing an alert signal if the duration of the sedentary state exceeds a predetermined time budget. For example, an alert can be issued, if the subject, such as a pregnant woman, is standing for too long. It should be noted, that the time budget does not have to be expended at once. Advantageously, a standing time budget can be set for a predetermined period of time such as a standing time budget per day. Hence, different periods wherein the device determines that the subject is standing can be accumulated even though these periods of one sedentary state are interrupted by other sedentary states or activities such as walking. Different budgets can be set for different states. It should be noted that the timing unit and/or alert unit can be implemented together with one or more further functional units of the apparatus for determining sedentary states of a subject as one physical entity or alternatively be implemented as separate units.

In an embodiment the predetermined time budget is determined based on at least one of user characteristics, age, gender, pregnancy status, family history, edema varicose veins problems, and/or occupation. Advantageously, the predetermined time budget can be adjusted according to the needs and medical situation of the subject. For example, a lower predetermined time budget can be assigned to a subject with a family history of lower limb problems.

In an embodiment the alert signal is at least one of an audible signal, a visual signal and a tactile signal. For example, assuming that the apparatus is implemented by a smart phone, a sound can be emitted as an audible signal, a message can be displayed on a display screen as a visual signal and/or a vibration can be effected as a tactile signal.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
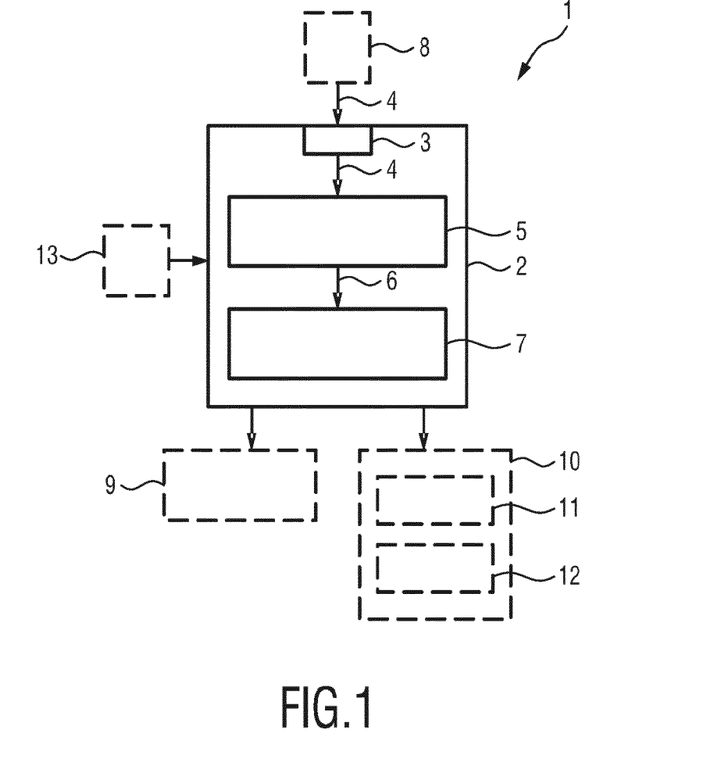
FIG. 1 shows a block diagram of a system for determining a sedentary state of a subject comprising an apparatus for determining a sedentary state of a subject according to an aspect of the present invention.

FIG. 1 shows an embodiment of a system for determining a sedentary state of a subject comprising an apparatus for determining a sedentary state of a subject. The system is therein denoted in its entirety with reference numeral 1. The apparatus for determining a sedentary state of subject is denoted with reference numeral 2.

The apparatus 2 for determining a sedentary state of the subject comprises a sensor interface 3 for obtaining a movement signal 4 indicative of a movement of the subject; an extraction unit 5 for extracting a signal feature 6 indicative of postural control oscillations of the subject from the movement signal; and a classifier 7 for classifying a sedentary state of the subject based on the signal feature 6 indicative of postural control oscillations of the subject.

The system 1 for determining a sedentary state of a subject can further comprise a movement sensor 8 for providing the movement signal 4 to the sensor interface 3 of the apparatus 2 for determining a sedentary state of the subject. Optionally, the sensor interface 3 can process the movement signal 4 received from the movement sensor 8 in order to provide a pre-processed movement signal to the extraction unit 5. Pre-processing can comprise steps such as analog-to-digital conversion, initial filtering and resampling.

The system 1 for determining a sedentary state of a subject can further comprise a storage unit 9. The storage unit 9 can for example store data relating to the movement signal 4, extracted signal features 6 indicative of postural control oscillations of the subject, and/or data relating to a sedentary state of the subject as provided by the classifier 7. The data can be stored for a subsequent analysis or offline processing. The data can be fed directly to a further module that can be suitable for real-time or near real-time intervention.

The system 1 for determining a sedentary state of a subject can further comprise an output unit 10 for providing one or more of the sedentary states of the subject from the classifier 7, the signal feature 6 indicative of postural control oscillations of the subject from the extraction unit 5 or the movement signal 4. The output unit 10 can be a one- or bidirectional interface such as an external world communication component or device.

In a practical embodiment, the apparatus for determining a sedentary state of subject 2 can be a sensor device or part of a sensor device, e.g. a wrist-mounted sensor device or smartwatch. A smartwatch or smartphone can also serve as an output unit 10. The determination of a sedentary state of a subject can be performed internally by a device such as a smartwatch which can optionally provide feedback to the subject. However, a movement signal or a determined sedentary state can also be sent to an output unit such as a smartphone for visualization or other presentation to a user.

The output unit 10 can comprise a timing unit 11 for determining a duration of a sedentary state and can further comprise an alert unit 12 for providing an alert signal if the duration of the sedentary state exceeds a predetermined time budget. For example, an alert can be issued if the subject is standing for too long. For example, a pregnant woman could be provided with a notification that she has been standing for a certain amount of time and that she might want to sit down or lie down. An alert according to this aspect of the present invention can serve as a preventive measure to reduce a risk of problems related to the lower limbs such as varicose veins. The timing unit 11 and/or the alert unit can be a part of the apparatus 2 for determining a sedentary state of the subject, can be part of the output unit 10 or a separate part of the system 1 for determining a sedentary state of the subject.

The system 1 for determining a sedentary state of a subject can further comprise an optional input unit 13. The input unit 13 and/or the output unit 10 can provide a user interface for the system 1 and/or the apparatus 2. The input unit 13 can be used to provide, for example, information about user characteristics, age, gender, pregnancy status, family history, edema and/or varicose veins problems of the subject. Such information can be considered in determining thresholds for the extraction of signal feature indicative of postural control oscillations of the subject by the extraction unit 5 and/or for classifying a sedentary state of the subject by the classifier 7. Furthermore, the input can also be provided to the alert unit 12 in order to adjust an alert threshold such as a predetermined time budget before issuing an alert and the type of an alert such as an audible signal, a visual signal and/or a tactile signal.

Figure 2:
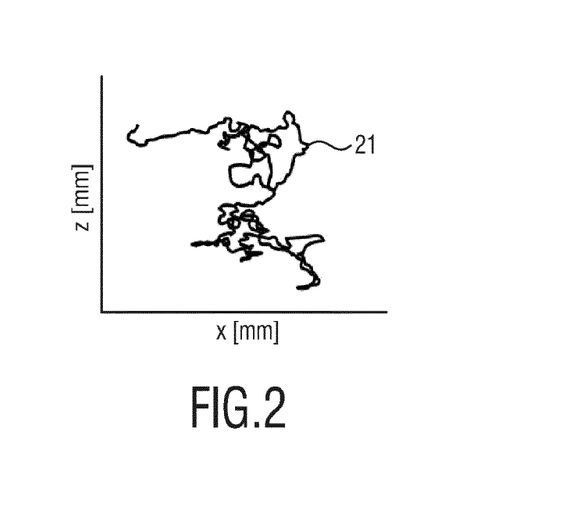
FIG. 2 shows a graph of postural control oscillations of a subject.

FIG. 2 shows an exemplary graph of postural control oscillations in a two-dimensional coordinate system. The graph depicts the oscillatory movements 21 of a center of mass of the subject due to postural control. Postural control oscillations as used herein can refer to a balancing movement, in particular a balancing movement about a mean value. As used herein, postural control oscillation is explicitly not limited to an ideal periodic sinusoidal oscillation in a strict mathematical sense. For evaluating postural control oscillations, it is not necessary to know an absolute position or orientation of the sensor in space. An advantage of said subtle subconscious postural control oscillations is that they can be sensed at a larger variety of body positions including but not limited to a hip region, chest region, arms, wrist, head and upper leg region. In a preferred embodiment, the movement sensor can be an accelerometer, which is co-integrated with a smartphone that can be worn in one's pocket. A main advantage of the apparatus for determining a sedentary state according to an aspect of the present invention is that it does not require knowing the orientation of the sensor in space up front and that it can be used for several wearing positions.

Figure 3:
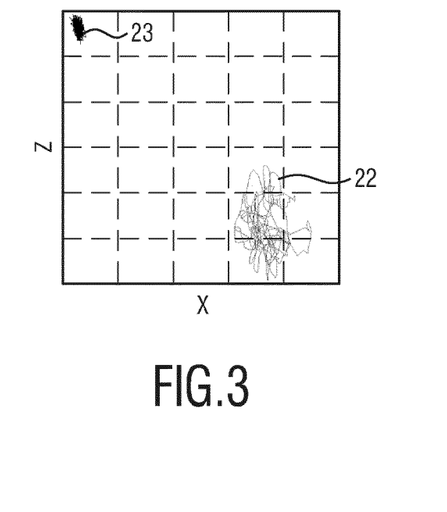
FIG. 3 shows a statokinesiogram of postural control oscillations while sitting and standing measured by means of a force plate.

FIG. 3 shows a statokinesiogram showing the center of mass oscillations due to postural control which prevent the person from falling. The horizontal axis is denoted with x and refers to oscillations along a sagittal axis. The vertical axis is denoted with z and refers to postural control oscillations along a coronal axis. However, it is to be noted, that the embodiment is not limited to a particular orientation of the sensor. A one, two, or three-dimensional accelerometer could be used as well as other sensors for sensing a movement of the body. The range of these postural control oscillations can be around 10 mm. However, the absolute value depends on user characteristics such as age, gender and fitness as well as a location or wearing position of the sensor on the body. Thresholds can be dependent on a wearing position and can advantageously be adjusted depending on the wearing position. Postural control oscillations can, for example, cause a higher movement signal amplitude at a hip or head region compared to a sensor worn on the wrist. For example a sensor worn clipped on a belt will be relatively close and connected to the center of mass.

Referring again to FIG. 3, the inventors have recognized that postural control oscillations while standing 22 show a larger spread than postural control oscillations while sitting 23. Correspondingly, postural control oscillations while lying can show a further reduced spread. In an embodiment, the classifier 7 may only distinguish between the sedentary state standing on the one hand and sitting or lying as a combined second sedentary state on the other hand. This reduces the complexity and can be sufficient, since several problems related to the lower limbs only occur while standing. In this case it is not necessary to further distinguish between sitting and lying.

A movement sensor 8 can either be placed on a body location where the postural control oscillations are taking place, or in a place, not necessarily on the user's body, where these oscillations can still be observed, such as on the ground by means of force plate as in FIG. 3 or using insole pressure sensors. Optionally, a camera can be used as a movement sensor for detecting postural control oscillations of the subject.

Figure 4:
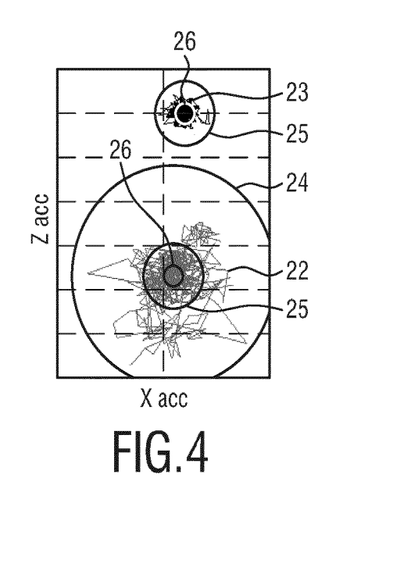
FIG. 4 shows a graph of postural control oscillations while sitting and standing measured by means of an accelerometer.

FIG. 4 shows a graph wherein an accelerometer is used as the movement sensor 8 for providing a movement signal 4 indicative of a movement of the subject to the sensor interface 3 of the apparatus 2 for determining a sedentary state of the subject as, for example, illustrated in FIG. 1. FIG. 4 depicts acceleration data in a transverse plane of the subject. The horizontal axis denotes an acceleration in a sagittal axis by Xacc. The vertical axis denotes an acceleration in a coronal axis by Zacc. The acceleration data serves as the movement signal 4. As shown in FIG. 4, a movement signal of a subject while standing 22 and sitting 23 can be clearly distinguished in that the acceleration while standing 22 shows a much broader signal spread than the acceleration while sitting 23. The data in FIG. 4 was obtained with a three-dimensional accelerometer and the coordinate system of the accelerometer was rotated to have an acceleration along the Y axis parallel to a gravity vector. Assuming that the user is standing or sitting upright, the gravity vector would thus be perpendicular to the transverse plane.

In the embodiment described with reference to FIG. 4, the extraction unit 5 can be configured to discard signal portions of the accelerometer signal or acceleration values that exceed a voluntary movement threshold 24, which is exemplarily indicated as a circle with a first radius around a center of the measured accelerations while standing 22. In order to distinguish between standing 22 and sitting 23, the classifier 7 for classifying a sedentary state of the subject can be configured for classifying the sedentary state as standing, as a first sedentary state, if the signal feature indicative of postural control oscillations of the subject is larger or equal to a first predetermined threshold. The first predetermined threshold is indicated by a circle 25 with a second predetermined radius around an average value of the respective acceleration values while standing 22 or sitting 23. It should be noted that a size of the clouds corresponding to the respective acceleration values can be seen as representative of the motion, whereas the absolute position of the clouds or circles is not necessarily relevant. For example, an absolute position can rather be attributed to an orientation or position of the sensor rather than a movement due to postural control oscillations. A bias on Xacc and/or Zacc can be omitted for the assessment of postural control oscillations. The classifier 7 can be configured for classifying the sedentary state as sitting as the second sedentary state, if the signal feature indicative of postural control oscillations of the subject is smaller than the first predetermined threshold. Optionally, there can be a second predetermined threshold, indicated as a circle 26 with a third radius around the average of the measured acceleration values.

Figure 5:
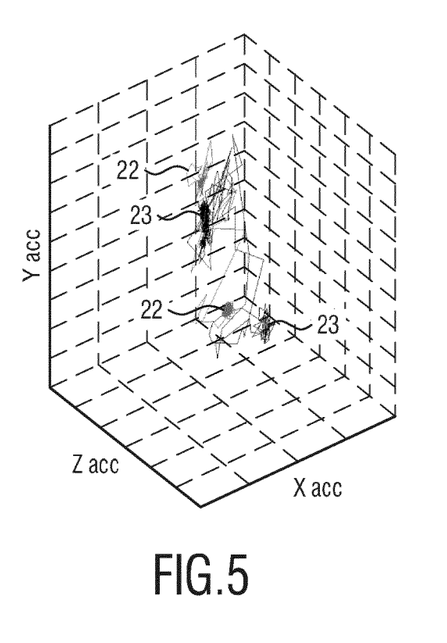
FIG. 5 shows a three-dimensional graph of raw accelerometer data while sitting and standing.
Figure 6:
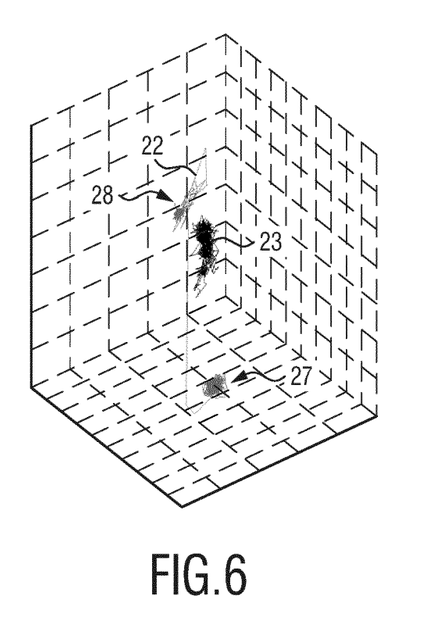
FIG. 6 shows a three-dimensional graph of processed accelerometer data while sitting and standing wherein voluntary movements have been removed.

FIG. 5 and FIG. 6 show three-dimensional graphs of acceleration signals as movement signals 4 derived from a three-dimensional accelerometer as a movement sensor 8. In this embodiment, the data was acquired with the accelerometer positioned at a wrist of the subject. The graphs depict the accelerations in x-, y- and z-direction, denoted by Xacc, Yacc and Zacc. FIG. 5 shows raw acceleration values as obtained from the movement sensor for standing 22 and sitting 23. FIG. 6 shows a processed version of the signals shown in FIG. 5, wherein the extraction unit 5 for extracting a signal feature indicative of postural control oscillations is further configured for determining signal windows in a movement signal indicative of voluntary movements and to discard the signal windows that are indicative of voluntary movements. In order to filter out voluntary movements, which would be read as standing because the high variance in the signal, prior to oscillations determination, the signal is windowed and high variance windows are discarded. Hence, signal portions of the movement signal wherein the subject is not inactive can be discarded. For example, signal portions that exceed a voluntary movement threshold as exemplarily indicated by circle 24 in FIG. 4 can be discarded. In other words, for example, a distinction between a voluntary movement and a sedentary condition can be seen as a first step or pre-processing step which can be done by a second classifier. The second classifier can be part of the extraction unit 5. This second classifier can be mainly based on a range of the acceleration signal. For example, approaches known from activity monitors for determining a voluntary activity such as walking, running or cycling can be used. In a subsequent step, the classifier 7 for classifying a sedentary state of the subject based on the signal feature indicative of postural control oscillations of the subject start its work for classifying the different sedentary conditions such as standing, sitting and/or lying. Thus, only windows without voluntary movements are considered for postural control oscillations determination based on FIG. 6.

FIG. 6 illustrates the advantage of filtering out voluntary movements from the raw acceleration data of FIG. 5 by comparing the raw data in FIG. 5 with the processed data after filtering in FIG. 6. FIG. 6 shows an example, wherein, at first sight, it may not be obvious, that the standing postural control oscillations 22 are greater than the postural control oscillations for sitting 23. However, when computing, for example, the sum of the distances of every point from the center of a cloud, to which that point belongs, for standing, this results in a higher value for postural control oscillations 22 while standing. The data depicted in FIG. 6 illustrates a scenario, wherein the movement sensor 8 was worn at the wrist of the user and the user moved his arm from a first position towards a second position with different mean acceleration values. FIG. 6 thus depicts a first cloud 27 and a second cloud 28 of values for the first and second position of the wrist respectively. The signal feature indicative of postural control oscillations of the subject can be determined separately and transitions between the different positions can be discarded.

It should be noted, that FIGS. 3 to 6 illustrate determining a sedentary state of the subject by distinguishing between standing and sitting/lying. However the same concept can be applied to further distinguish for example between sitting and lying.

An exemplary extraction of a signal feature indicative of postural control oscillations of the subject from a movement signal and classification will be now described for an accelerometer-based device worn at a belt or wrist position respectively.

In a first example, the movement sensor is worn at the belt wherein components of the acceleration signal are predominantly in an x- and z-direction, i.e. substantially perpendicular to a gravity vector in negative y-direction. In a first step, the following quantities can be calculated:

$$Xfactor = \frac{\sum_{j=1}^{length(Xacc)} |Xacc(j) - \text{mean}(Xacc)|}{length(Xacc)}$$

$$Zfactor = \frac{\sum_{j=1}^{length(Zacc)} |Zacc(j) - \text{mean}(Zacc)|}{length(Zacc)},$$

wherein Xacc denotes an acceleration along the x-axis, Zacc denotes an acceleration along the z-axis, and length (Xacc) refers to a length such as a length of a vector of measurement values. The Xfactor can thus refer to a term that sums an absolute value of the differences between the X accelerations and their mean values. The same applies to the Zfactor. It should be noted, that such a vector of measurement values can also refer to a measurement vector after pre-processing or filtering, thus a vector of reduced length, wherein some of the original measurement signal has been discarded. For example, an acceleration signal is windowed and, thanks to its mean value and length in the window, the Xfactor and/or Zfactor can be calculated. It is also possible that the signals or vectors of an acceleration along the x-axis and an acceleration along the z-axis can have different lengths. In an alternative embodiment, the Xfactor or Zfactor can also refer to a standard deviation or variance of the signal or a portion of the signal for example a cloud as described with reference to FIG. 6.

Based on the Xfactor and Zfactor, a combined value can be determined for example by calculating:

$$XZ_{sitting} = Xfactor_{sitting} + Zfactor_{sitting}$$

$$XZ_{standing} = Xfactor_{standing} + Zfactor_{standing},$$

wherein $XZ_{sitting}$ and $XZ_{standing}$ refer to the sum of the contribution of the previous two factors Xfactor and Zfactor in case of sitting and standing.

The expected acceleration behavior for postural control oscillations for an accelerometer arranged at a belt position of the subject is that $XZ_{standing}$ as the signal feature indicative of postural control oscillations of the subject while standing is larger than $XZ_{sitting}$ as the signal feature indicative of postural control oscillations of the subject while sitting, such that $XZ_{standing} > XZ_{sitting}$. The values $XZ_{standing}$ and $XZ_{sitting}$ thus refer to the contribution of the previous two factors for the X and Z axis respectively in case of sitting and standing. The signal feature indicative of postural control oscillations of the subject, such as the quantity XZ as described above, is provided to the classifier 7 for classifying a sedentary state. For example, the XZ is compared to a predetermined threshold. If the XZ value is larger or equal to a first predetermined threshold the first sedentary state is classified as standing, or whereas if the XZ is smaller than the first predetermined threshold, the sedentary state is classified as sitting and/or lying.

In an embodiment, the extraction unit for extracting a signal features indicative of postural control oscillations can be configured for windowing the movement signal and to discard signal windows that are indicative of voluntary movements and/or noise or other disturbances. Reference is again made to an exemplary embodiment, wherein a three-dimensional accelerometer is used as the movement sensor for obtaining the movement signal. In a first step an acceleration magnitude is determined by calculating $$AccMagn = \sqrt{Xacc^2 + Yacc^2 + Zacc^2},$$

wherein AccMagn refers to a magnitude of the acceleration vector, Xacc refers to an acceleration along the x-axis, Yacc refers to an acceleration along the y-axis and Zacc refers to an acceleration along the z-axis.

The movement signal is considered as an acceleration vector which is segmented in several segments of a predetermined length and the acceleration vector is windowed for every segment by the following condition:

$$IF \frac{std[AccMagn(\text{interval})]}{mean[AccMagn(\text{interval})]} < \text{threshold THEN } Xsegment_i = Xacc(\text{interval})$$

Thereby, a pre-processed signal vector can be built for only those intervals or segments of the acceleration signal that fulfill the aforementioned IF condition. Segments which do not fulfill the IF condition can be discarded. If the threshold condition is not satisfied, the algorithm can jump directly to the next window of the signal.

For each $Xsegment_i$ vector, a corresponding $Xfactor_i$ can be determined by calculating:

$$Xfactor_i = \frac{\sum_{j=1}^{length(Xsegment_i)} |Xsegment_i(j) - mean(Xsegment_i)|}{length(Xsegment_i)}$$

The Xfactor(i) can thus refer to a term that sums an absolute value of the differences between the X accelerations of segment i and their mean values The Xfactors for each of said segments can be combined as a total Xfactor-TOT by calculating $$XfactorTOT = \sum_{i=1}^{N\,segment} Xfactor_i.$$

The XfactorTOT thus provides a sum of the Xfactors calculated for each segment. The processing for the y- and z-axis can be performed analogously.

Based thereon, an XYZ value can be determined for sitting and standing by calculating:

$$XYZ_{sitting} = Xfactor_{sitting} + Yfactor_{sitting} + Zfactor_{sitting}$$

$$XYZ_{standing} = Xfactor_{standing} + Yfactor_{standing} + Zfactor_{standing}.$$

$XYZ_{standing}$ and $XYZ_{sitting}$ respectively refer to the sum of the contribution of the previous three factors in case of sitting and standing. The expected acceleration behavior of an accelerometer at the wrist position is thus that $XYZ_{standing}$ as the signal feature indicative of postural control oscillations of the subject while standing is larger than $XYZ_{sitting}$ as the signal feature indicative of postural control oscillations of the subject while sitting, such that $XYZ_{standing} > XYZ_{sitting}$.

The signal feature indicative of postural control oscillations of the subject, such as the quantity XYZ as described above, can again be provided to the classifier 7 for classifying a sedentary state as described above for the quantity XZ in the two-dimensional case.

Figure 7:
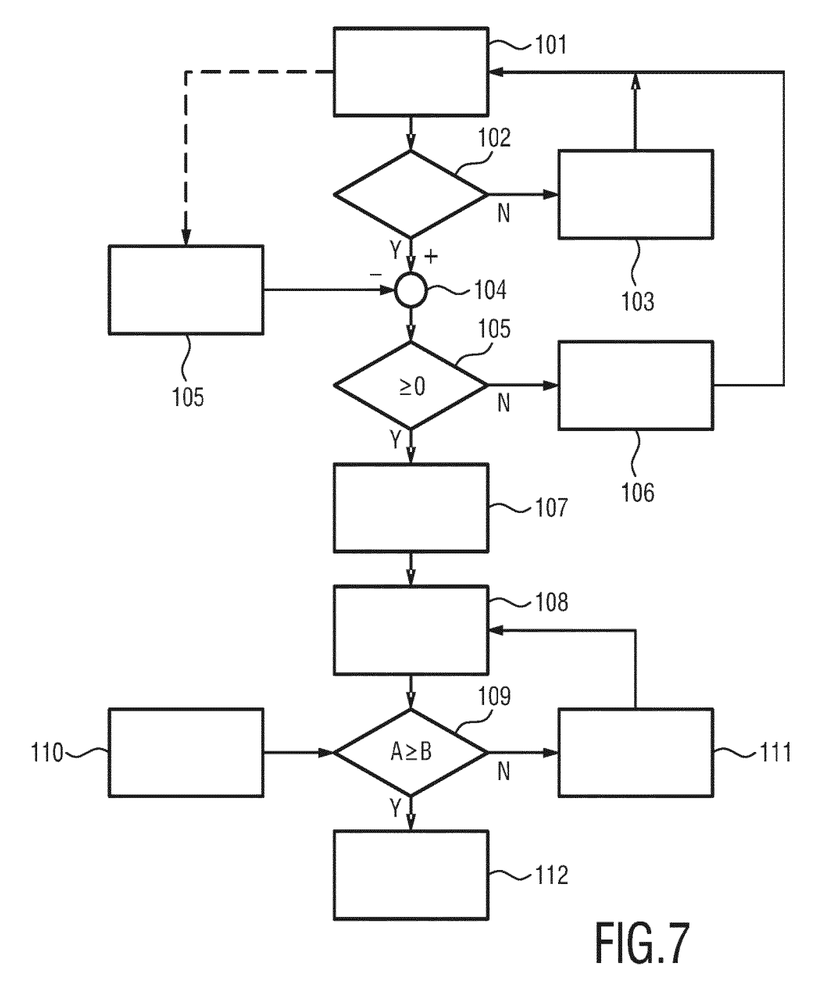
FIG. 7 shows a flow chart of an embodiment.

FIG. 7 illustrates an embodiment of a flow chart referring to an apparatus 2 for determining a sedentary state of a subject further comprising a timing unit 11 for determining a duration of a sedentary state and an alert unit 12 for providing an alert signal if the duration of the sedentary state exceeds a predetermined time budget.

In a first step 101 a movement signal indicative of a movement of the subject is obtained from a movement sensor 8 via a sensor interface 3. The movement signal is then provided to a pre-processing block 102 to filter out voluntary movements for example by determining signal windows of a movement signal indicative of voluntary movements and discarding the signal windows that are indicative of voluntary movements. For example, if an amplitude and/or a variance of the movement signal exceeds a predetermined voluntary movement threshold, the respective portions of the movement signal are discarded 103 as non-reliable data and are not used for determining a sedentary state of the subject. If the preprocessing block 102 is passed, the respective signal portion is provided to a summation block 104, wherein a predetermined standing threshold value 105 can be subtracted from the signal. The predetermined standing threshold value 105 can optionally be based on a signal obtained from block 101, for example in a self-learning fashion, in particular on previous movement signals. In that case based on a distribution of the sensor input signal and e.g. an expected amount of time a person is sitting/standing/lying down the thresholds can automatically be determined. The predetermined standing threshold 105 can also refer to a history determined standing threshold, for example based on previous measurements of the same subject or data available from a peer group of the subject which shares several characteristics for example in terms of age, gender, health status and/or fitness.

The predetermined standing threshold 105 can, for example, be determined in two ways. As a first option, the user calibrates the system. When the device is started this asks to the user to stay in positions classified by the device for a certain amount of time in a specific order. As a second option, the device is configured to auto-calibrate itself. For example after a day of use the device auto-sets a threshold clustering of an inactive period. A center of the cluster with lower feature values corresponds to sitting and a second cluster with higher feature values corresponds to standing, in case of binomial classification between sitting and standing. However, a similar procedure using one more cluster can be used if also lying is present. A threshold between the behaviors could be taken as the mean between the two centers of the clusters.

The thresholds, such as a first threshold to distinguish standing from sitting and optionally a further threshold to distinguish sitting from lying can also be set for example by the manufacturer after a data analysis on large amount of data from previous measurements. The manufacturer can implement one or more thresholds before the device/system is released. The threshold can be dependent on the sedentary activity to recognize, but it can depend also on the one or more user parameters, such as age, gender, weight, height.

As indicated above, the thresholds can also be calculated from an automatic calibration procedure. For example, initially the device/system does not have any threshold value implemented. After one or more days of use, the data relative to inactive or sedentary periods are stored and clustered. Before the clustering an outlier removal algorithm can also be implemented. The cluster procedure can be implemented to create two or more clusters of oscillation features that are assigned to the sedentary activities that the device intends to classify. Such an unsupervised assignation of clusters to certain classes or states can be possible due to the nature of features. For example, in case of three classes, a lower oscillation feature cluster can be assigned to lying, a middle cluster to sitting and a higher to standing.

Moreover, one or more different approaches such automatic calibration, calibration by the user and thresholds set by the manufacturer can advantageously be combined.

Following the summation block 104, the signal is provided to the decision block 105 to determine whether the signal is larger or equal to 0. If the received signal is not larger or equal to 0, the signal can be classified as sitting or lying 106. If the signal is larger or equal to 0 is can be classified as standing 107.

Episodes when the user is standing can be accumulated for determining a duration of a standing time A in step 108. The duration of the sedentary state standing can be determined by a timing unit 11 as illustrated in the block diagram shown in FIG. 1. In decision block 109, the standing time A can be compared to a predetermined standing time budget B provided by block 110. If the determined standing time A is smaller than the standing time budget B, the system can optionally indicate the standing time and/or a remaining standing time budget based on a difference of standing time budget B and the determined standing time A or simply do nothing in step 111. However, if the determined standing time A is larger or equal to the standing time budget B, the system 1 for determining a sedentary state of a subject can provide an alert signal and optionally provide an alarm output 112.

In this embodiment, each user can have a standing still budget, for example a total amount of time of for example one hour, that the user can stand still without introducing a health risk. The standing still budget 110 can be personalized according to user's characteristics such as age, gender, pregnancy status, family history or edema and varicose veins problems and the like. Corresponding information can be received by the system 1 via the input unit 13. If the actual measured standing still time 108 exceeds the predetermined time budget 110, the user can get a notification 112 which can be of any kind and form such as auditory visual and/or vibration.

Figure 8:
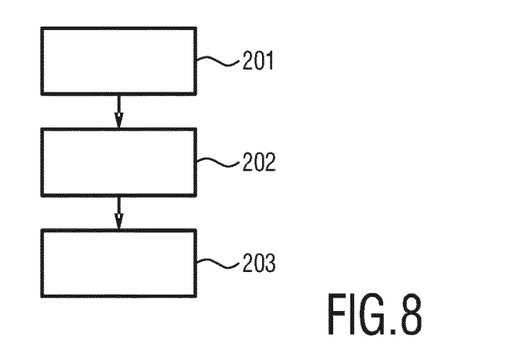
FIG. 8 shows a flow chart of a method for determining a sedentary state of a subject according to an aspect of the present invention.

FIG. 8 illustrates a method for determining a sedentary state of a subject according to an aspect of the present invention. In step 201, a movement signal indicative of a movement of the subject is obtained. In step 202 a signal feature indicative of postural control oscillations of the subject is extracted from the movement signal. In step 203 a sedentary state of the subject is classified based on the signal feature indicative of postural control oscillations of the subject.

Advantageously, the aforementioned embodiment can be used for prevention purposes in particular for pregnant women who are at high risk of edema and developing varicose veins problems when standing still and for workers with predominantly standing jobs such as hairdressers and production workers who have an increased risk of problems of the lower limbs.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An apparatus for determining a sedentary state of a subject comprising:
   a sensor interface for obtaining, via a sensor, a movement signal indicative of a movement of the subject;
   an extraction unit configured to:
   filter out portions of the movement signal corresponding to voluntary center-of-mass oscillations to obtain a filtered movement signal; and
   extract, from the filtered movement signal, a signal feature indicative of involuntary center-of-mass oscillations associated with postural muscles of the subject, the signal feature comprising indications of involuntary center-of-mass postural corrections of the subject; and a classifier configured to classify the sedentary state of the subject based on the indications of involuntary center-of-mass postural corrections of the subject.

2. The apparatus according to claim 1, wherein classifying the sedentary state of the subject comprises a classification into at least one of standing, sitting and/or lying.

3. The apparatus according to claim 1, wherein the classifier is configured for classifying the sedentary state of the subject as a first sedentary state of the subject, when the signal feature indicative of involuntary center-of-mass postural corrections of the subject is larger or equal to a first predetermined threshold, or as a second sedentary state of the subject, when the signal feature indicative of involuntary center-of-mass postural corrections of the subject is smaller than the first predetermined threshold.

4. The apparatus according to claim 1, wherein said signal feature indicative of involuntary center-of-mass oscillations associated with postural muscles of the subject comprises at least one of an oscillation amplitude, an oscillation variance, and a sum of distances of values of the filtered movement signal from a center of a cloud of said values of the filtered movement signal.

5. The apparatus according to claim 1, wherein the signal feature indicative of involuntary center-of-mass oscillations associated with postural muscles of the subject is extracted by determining signal windows in the movement signal indicative of voluntary movements; and discarding the signal windows that are indicative of voluntary movements.

6. The apparatus according to claim 5, wherein the extraction unit is configured to determine signal windows in the movement signal indicative of voluntary movements by determining when an amplitude and/or variance of the movement signal exceeds a predetermined voluntary movement threshold and/or by determining when a spectral content of the movement signal corresponds to a voluntary movement spectrum.

7. The apparatus according to claim 1, wherein the extraction unit is configured to determine a gravity vector and to determine the signal feature indicative of postural control oscillations that are perpendicular to the gravity vector.

8. The apparatus according to claim 1, wherein the extraction unit extracts the signal feature by extracting, based on an adaptive threshold, the signal feature indicative of involuntary center-of-mass oscillations associated with postural muscles of the subject from the filtered movement signal.

9. The apparatus according to claim 1, further comprising:
a timing unit configured to determine a duration of the sedentary state of the subject; and
an alert unit configured to provide an alert signal when the duration of the sedentary state of the subject exceeds a predetermined time budget.

10. The apparatus according to claim 9, wherein the predetermined time budget is determined based on at least one of user characteristics, age, gender, pregnancy status, family history, edema, varicose veins problems, and/or occupation.

11. The apparatus according to claim 9, wherein the alert signal is at least one of an audible signal, a visual signal and a tactile signal.

12. The apparatus according to claim 1, wherein the involuntary center-of-mass oscillations are produced by a skeletal muscular system of the subject to keep the center of mass of the subject within a base of support.

13. The apparatus according to claim 1, wherein the involuntary center-of-mass postural corrections of the subject are subconscious movements of the subject in the sedentary state.

14. The apparatus according to claim 1, wherein the involuntary center-of-mass postural corrections counteract a tendency of a body to move a center of gravity outside a base of support.

15. The apparatus according to claim 1, wherein the involuntary center-of-mass postural corrections comprise contractions and relaxations of postural muscles.

16. The apparatus according to claim 15, wherein the contractions and relaxations of postural muscles counteract a tendency of a body to move the center of gravity outside a base of support.

17. A system for determining a sedentary state of a subject comprising:
a movement sensor for providing the movement signal; and
the apparatus according to claim 1.

18. A method for determining a sedentary state of a subject comprising:
obtaining, via a sensor, a movement signal indicative of a movement of the subject;
filtering out, via a processor, portions of the movement signal corresponding to voluntary center-of-mass oscillations to obtain a filtered movement signal;
extracting, via the processor, a signal feature indicative of involuntary center-of-mass oscillations associated with postural muscles of the subject from the filtered movement signal, the signal feature comprising indications of involuntary center-of-mass postural corrections of the subject; and
classifying, via the processor, the sedentary state of the subject based on the indications of involuntary center-of-mass postural corrections of the subject.

19. A computer program comprising program code means for causing a computer to carry out the steps of the method as claimed in claim 18 when said computer program is carried out on the computer.

* * * * *